United States Patent
Tilly et al.

(10) Patent No.: US 12,274,895 B2
(45) Date of Patent: Apr. 15, 2025

(54) ADAPTIVE DOSE ACCUMULATION ALGORITHM

(71) Applicant: Elekta AB (publ), Stockholm (SE)

(72) Inventors: David Andreas Tilly, Uppsala (SE); Peter Kimstrand, Uppsala (SE); Petter Ericson, Uppsala (SE); Nina Terese Tilly, Uppsala (SE)

(73) Assignee: Elekta AB (publ), Stockholm (SE)

( * ) Notice: Subject to any disclaimer, the term of this patent is extended or adjusted under 35 U.S.C. 154(b) by 361 days.

(21) Appl. No.: 17/757,749

(22) PCT Filed: Dec. 20, 2019

(86) PCT No.: PCT/EP2019/086664
§ 371 (c)(1),
(2) Date: Jun. 20, 2022

(87) PCT Pub. No.: WO2021/121622
PCT Pub. Date: Jun. 24, 2021

(65) Prior Publication Data
US 2022/0362582 A1    Nov. 17, 2022

(51) Int. Cl.
*A61N 5/10*    (2006.01)
*G16H 20/10*    (2018.01)
(Continued)

(52) U.S. Cl.
CPC ......... *A61N 5/1067* (2013.01); *A61N 5/1031* (2013.01); *A61N 5/1037* (2013.01);
(Continued)

(58) Field of Classification Search
CPC ........ G16H 20/40; G16H 30/40; G16H 20/10; G16H 50/20; G16H 50/50; G16H 40/67;
(Continued)

(56) References Cited

U.S. PATENT DOCUMENTS 10,350,438 B2    7/2019  Brooks
10,456,600 B2 *  10/2019 Owens ................. A61N 5/1081
(Continued)

FOREIGN PATENT DOCUMENTS

CN    102549586    7/2012
CN    106456064    2/2017
(Continued)

OTHER PUBLICATIONS

"International Application Serial No. PCT/EP2019/086664, International Search Report mailed Aug. 28, 2020", 3 pgs.
(Continued)

*Primary Examiner* — Irakli Kiknadze
(74) *Attorney, Agent, or Firm* — Schwegman Lundberg & Woessner, P.A.

(57) ABSTRACT

Techniques for adjusting radiotherapy treatment for a patient in real time are provided. The techniques include operations comprising: obtaining, during delivery of a radiotherapy treatment fraction to a patient, one or more images of the patient at a first rate; generating patient motion information at a second rate based on the one or more images obtained at the first rate; receiving, during delivery of the radiotherapy treatment fraction, radiotherapy treatment device settings at a third rate; computing, during delivery of the radiotherapy treatment fraction, dose delivered to the patient with a first level of accuracy based on the generated patient motion information and the radiotherapy treatment device
(Continued)

settings; and determining, during delivery of the radiotherapy treatment fraction, a real-time measure of accumulated dose delivered to the patient with a second greater level of accuracy than the first level of accuracy using one or more prior dose computations.

20 Claims, 6 Drawing Sheets

(51) Int. Cl.
  *G16H 20/40* (2018.01)
  *G16H 30/40* (2018.01)
(52) U.S. Cl.
  CPC .......... *A61N 5/1045* (2013.01); *A61N 5/1071* (2013.01); *G16H 20/10* (2018.01); *G16H 20/40* (2018.01); *G16H 30/40* (2018.01); *A61N 2005/1034* (2013.01); *A61N 5/1068* (2013.01); *A61N 2005/1072* (2013.01)
(58) Field of Classification Search
  CPC ...... G16H 50/70; G16H 30/20; A61N 5/1067; A61N 5/1045; A61N 5/1037; A61N 5/1031; A61N 5/1071; A61N 2005/1072; A61N 2005/1034; A61N 5/1068; A61N 5/1049; A61N 5/107; A61N 5/1038; A61N 2005/1087; A61N 5/1036; A61N 5/1081; A61N 5/1042; A61N 2005/1062; A61N 5/1039; A61N 5/103; A61N 5/1083; A61N 2005/1061; A61N 2005/1074; A61N 2005/1055; A61N 2005/1054; A61N 5/1064; A61N 2005/1058; A61N 2005/1052; A61N 5/1075; A61N 5/1084; A61N 5/10; A61N 2005/109; G06T 17/00; G06T 7/0016; G06T 2210/41; G06T 2207/30096; G06T 7/0012; G06T 2207/10144; G06T 2207/30168; G06T 2207/20081; G06T 2207/10081; A61B 5/7267; A61B 6/4014; A61B 90/37; A61B 34/25; A61B 2090/374; A61B 34/30; A61B 2034/256; A61B 6/58; A61B 6/488; A61B 6/542; A61B 6/032; A61B 6/545; A61B 6/037; A61B 6/5217; G06N 20/00; G06N 3/08; G06N 20/20; G01R 33/3806; G01R 33/4808; G01T 1/20; G01T 1/023; G01T 1/22; G01T 7/005; G01T 1/2002; G01T 1/1603; G06V 10/25; G06V 10/82
  USPC .......................................................... 378/65
  See application file for complete search history.

(56) References Cited

U.S. PATENT DOCUMENTS

| | | | |
|---|---|---|---|
| 2013/0188856 A1* | 7/2013 | Adler, Jr. ............... | A61B 6/463 382/132 |
| 2016/0038767 A1* | 2/2016 | Wiersma .............. | A61N 5/1031 378/204 |
| 2018/0280731 A1* | 10/2018 | Oldham ................. | A61N 5/103 |
| 2018/0345042 A1 | 12/2018 | Voronenko et al. | |
| 2019/0091487 A1 | 3/2019 | Pal et al. | |
| 2019/0329071 A1* | 10/2019 | Grittani ................ | A61N 5/1075 |
| 2020/0075148 A1* | 3/2020 | Nguyen ................. | G16H 20/10 |
| 2021/0138267 A1* | 5/2021 | Nord ....................... | A61N 5/103 |

FOREIGN PATENT DOCUMENTS

| | | |
|---|---|---|
| CN | 110366757 | 10/2019 |
| CN | 115004311 | 9/2022 |

OTHER PUBLICATIONS

"International Application Serial No. PCT/EP2019/086664, Written Opinion mailed Aug. 28, 2020", 9 pgs.
Jiang, Steve B, et al., "Removing the effect of statistical uncertainty on dose-volume histograms from Monte Carlo dose calculations", Physics in Medicine and Biology, 45(8), (2000), 2151-2161.
Kamerling, Cornelis PH., et al., "Online dose reconstruction for tracked volumetric arc therapy: Real-time implementation and offline quality assurance for prostate SBRT", Medical Physics, 44(11), (Nov. 2017), 5997-6007.
Kamerling, Cornelis PH., et al., "Real-time 4D dose reconstruction for tracked dynamic MLC deliveries for lung SBRT", Medical Physics, 43(11), 6072-6081, (2016), 11 pgs.
Li, Haisen S, et al., "Direct dose mapping versus energy/mass transfer mapping for 4D dose accumulation: fundamental differences and dosimetric consequences", Physics in Medicine and Biology, 59(1), (2014), 173-188.
Poulsen, Per Rugaard, "A method of dose reconstruction for moving targets compatible with dynamic treatments", Medical Physics, 39(10), (2012), 6237-6246.
Skouboe, Simon, et al., "First clinical real-time motion-including tumor dose reconstruction during radiotherapy delivery", Radiotherapy and Oncology, 139, (2019), 66-71.
"European Application Serial No. 19831728.1, Response to Communication pursuant to Rules 161 and 162 filed Jan. 25, 2023", 19 pgs.
"Chinese Application Serial No. 201980103469.9, Office Action mailed Sep. 26, 2024", w o English translation, 10 pgs.

\* cited by examiner

ADAPTIVE DOSE ACCUMULATION ALGORITHM

PRIORITY APPLICATIONS

This application is a U.S. National Stage Filing under 35 U.S.C. § 371 from International Application No. PCT/EP2019/086664, filed on Dec. 20, 2019, and published as WO2021/121622 on Jun. 24, 2021; the benefit of priority of which is hereby claimed herein, and which application and publication are hereby incorporated herein by reference in its entirety.

TECHNICAL FIELD

This disclosure relates generally to radiation therapy or radiotherapy. More specifically, this disclosure relates to systems and methods for computing accumulated dose in real-time during a radiotherapy treatment fraction.

BACKGROUND

Radiotherapy is used to treat cancers and other ailments in mammalian (e.g., human and animal) tissue. Radiotherapy includes linear particle accelerator (LINAC)-based radiotherapy and circular particle accelerators (e.g., cyclotron, synchrotron, and synchrocyclotron). The direction and shape of the radiation beam should be accurately controlled to ensure a target tumour receives the prescribed radiation, and the placement of the beam should be such as to minimize damage to the surrounding healthy tissue including especially sensitive organs, often called the organ(s) at risk (OARs). Treatment planning can be used to control radiation beam parameters, and a radiotherapy device effectuates a treatment by delivering a spatially varying dose distribution to the patient according to a treatment plan.

Overview

In some embodiments, a computer-implemented method, transitory or non-transitory computer-readable medium, and a system comprising a memory and processor are provided for performing operations comprising: obtaining, by one or more processors, during delivery of a radiotherapy treatment fraction to a patient, one or more images of the patient at a first rate; generating patient motion information at a second rate based on the one or more images obtained at the first rate by sampling the one or more images at the second rate that is lower than the first rate; receiving, during delivery of the radiotherapy treatment fraction, radiotherapy treatment device settings at a third rate that is greater than the first rate; computing, during delivery of the radiotherapy treatment fraction, dose delivered to the patient with a first level of accuracy based on the generated patient motion information and the radiotherapy treatment device settings; and determining, at a rate lower than the first rate, during delivery of the radiotherapy treatment fraction, a real-time measure of accumulated dose delivered to the patient with a second greater level of accuracy than the first level of accuracy using one or more prior dose computations.

In some embodiments, the operations further include: determining a fourth rate at which the dose is computed and accumulated, the fourth rate being lower than the first rate; and setting the second rate at which the one or more images are sampled based on the fourth rate at which the dose is computed.

In some embodiments, generating the patient motion information comprises adjusting the second rate at which the collection of the one or more images is sampled to ignore and exclude a portion of the one or more images, obtained at the first rate, from the generated patient motion information.

In some embodiments, the dose is computed using an advanced Monte Carlo dose calculation technique resulting in a dose distribution with a noise level corresponding to the first level of accuracy.

In some embodiments, the dose is computed at a fourth rate such that each of a plurality of dose computations for the radiotherapy treatment fraction is output at the fourth rate, each of the plurality of dose computations individually having a level of accuracy lower than the second level of accuracy, and the operations further comprise: transforming each of the plurality of dose computation to a same frame of reference of a reference geometry and accumulating each of the plurality of dose computations at a respective increment, to determine the real-time measure of accumulated dose, wherein each increment of accumulation increases a level of accuracy of a dosimetric index.

In some embodiments, the second rate is set to a value that sufficiently resolves motion patterns of the patient, wherein the level of accuracy of each individual dose computation comprises an individual advanced Monte Carlo dose calculation, wherein the second level of accuracy comprises an accumulated three-dimensional (3D) Monte Carlo dose calculation.

In some embodiments, the dosimetric index includes at least one of a quantitative single measure extracted from a 3D dose distribution, a near-maximum dose, a near-minimum dose, or a measure of conformity between a dose distribution and a target volume.

In some embodiments, the dosimetric index includes a dose value histogram (DVH) or a DVH measure.

In some embodiments, the operations further comprise calculating the dosimetric index by extracting a subset of 3D portions of the accumulated 3D Monte Carlo dose calculation, the dosimetric index having a third level of accuracy greater than the first and second levels of accuracy.

In some embodiments, the operations further comprise compressing, into a single effective segment, the radiotherapy treatment device settings based on the second rate at which the patient motion information is generated, wherein the dose is computed based on the compressed radiotherapy treatment device settings.

In some embodiments, the radiotherapy treatment device settings received at the third rate comprises a set of updates to the radiotherapy treatment device settings performed during a given time interval of the radiotherapy treatment fraction corresponding to the third rate, further comprising aggregating into the single effective segment a total fluence delivered by a plurality of beam delivery segments.

In some embodiments, the single effective segment comprises a start and a stop position of every pair of beam limiting device (BLD) elements, wherein computing the effective segment comprises, for every pair of BLD elements, comprises operations for: obtaining all positions of the pair of BLD elements for each of the set of updates; identifying a maximum position of each pair of BLD elements in a current pair of BLD elements among the obtained positions in the set of updates; identifying a minimum position of each pair of BLD elements in the current pair of BLD elements among the obtained positions in the set of updates; assigning the minimum position as a starting position for each pair of BLD elements in the current pair of BLD elements; and assigning the maximum position as a stopping position for each pair of BLD elements in the current pair of BLD elements.

In some embodiments, the pair of BLD elements comprises at least one of a pair of jaws of a multi-leaf collimator (MLC) or a pair of leaves of the MLC, and the operations further comprise: determining a number of monitor units (MU) delivered for each of the set of updates; accumulating the determined number of MU for the set of updates to compute a total fluence; and assigning the accumulated MU to the effective segment.

In some embodiments, the operations further comprise generating, at a fourth rate, a visualization of dose accumulation based on the determined real-time measure of accumulated dose delivered to the patient during delivery of the radiotherapy treatment fraction.

In some embodiments, the visualization illustrates real-time progress of the radiotherapy treatment fraction, and the operations further comprise: obtaining a reference dosimetric index calculated based on a reference radiotherapy treatment plan; and presenting, in the visualization, the real-time progress by graphically displaying a same dosimetric index based on the accumulated dose relative to the reference dosimetric index.

In some embodiments, the operations further comprise gating or adjusting the radiotherapy treatment device settings based on the determined real-time measure of dose and one or more additional factors during delivery of the radiotherapy treatment fraction.

In some embodiments, the patient motion information is generated by: applying a patient motion model to one or more reference images of the patient to create a motion estimate; and deforming a patient anatomy to a current state using the motion estimate.

In some embodiments, the computed dose comprises a first computed dose corresponding to a first portion of the radiotherapy treatment fraction, further comprising denoising a differential dose volume histogram of the first computed dose while computing a second dose for a second portion of the radiotherapy treatment fraction.

The above overview is intended to provide an overview of subject matter of the present patent application. It is not intended to provide an exclusive or exhaustive explanation of the inventive subject matter. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
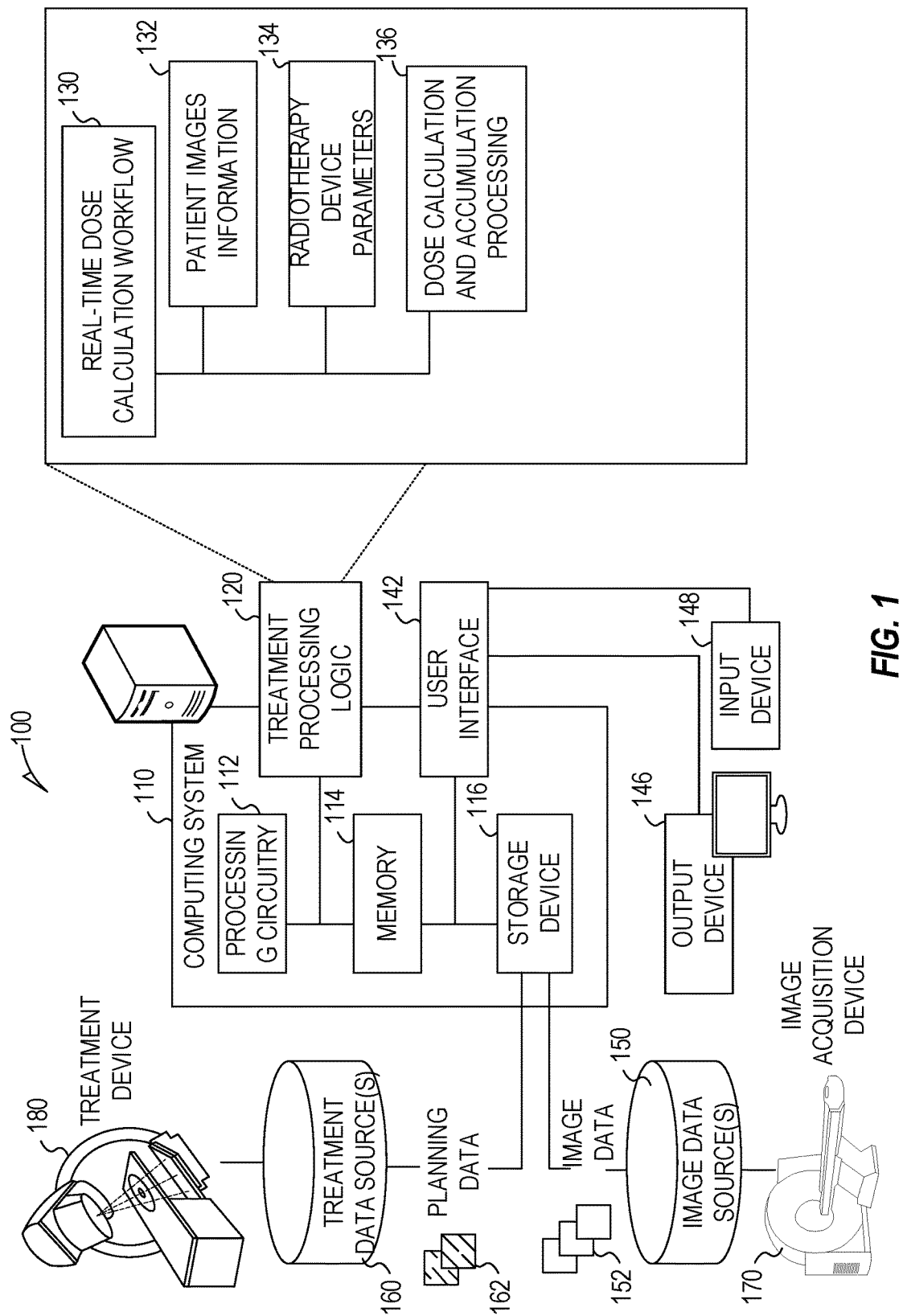
FIG. 1 is an illustrative radiotherapy system adapted for performing real-time dose calculations during a radiotherapy treatment fraction according to some examples.

The present disclosure includes various techniques to improve and enhance radiotherapy treatment by computing dose accumulation in real-time during a radiotherapy treatment fraction. Such real-time dose accumulation computations can be used as a quality assurance (QA) measure during the radiotherapy treatment session to reassure a user or operator that treatment is progressing according to the treatment plan. The disclosed techniques may be applicable to a variety of medical treatment and diagnostic settings or radiotherapy treatment equipment and devices.

Doses to vital organs and healthy tissue in radiotherapy treatments should be minimized due to the risk of serious injuries and late effects. However, treatment planning is normally performed prior to the patient's first treatment session, based on one or several image set/s of the patient (e.g., a snapshot in time of the patient). Specifically, the conventional way to deliver radiotherapy is to image the patient with computed tomography imaging (CT), magnetic resonance imaging (MRI), and/or positron emission tomography imaging (PET) days or even weeks before the treatment starts. Based on that one snapshot of the patient anatomy a treatment plan is created and the same plan is used through the entire treatment course. A treatment plan consists of several beam segments of different weights—cumulative metersets—delivered at discrete or continuous gantry angles with different multi-leaf collimator and jaw settings (i.e., beam limiting devices) shaping the fluence of the segments.

The treatment is delivered, based on the treatment plan, in several fractions (typically 5-40), most commonly one per day. One fraction takes in the order of minutes to deliver. The patient anatomy can change between fractions (inter-fraction) due to, for example, weight loss or by the fact that internal organs change shape and relative position, as well as within one fraction (intra-fraction) due to, for example, breathing. The standard way to ensure sufficient target dose coverage in spite of these uncertainties is to expand the irradiated volume with a margin. However, with large spatial uncertainties the margins may result in irradiation of a large volume of normal tissue, resulting in an increased risk of both early (e.g. inflammation of the skin, bladder or digestive tract) and late (e.g. fibrosis, atrophy, vascular damage, infertility, cognitive problems or secondary cancers) normal tissue complications.

The introduction of elaborated imaging possibilities at the treatment machine enables re-imaging of the patient in the treatment position right before delivery of each fraction. The treatment plan can then be adapted according to those daily images before delivery, which is known as online adaptive radiotherapy. Utilizing online adaptive techniques, inter-fraction changes in the anatomy can hence be considered and compensated for. However, intra-fraction changes still need to be addressed by adding margins to the target (tumour) volume. These margins might be made smaller than for conventional radiotherapy where a single treatment plan is used for the whole course of the treatment.

One way to implement the QA of a clinical treatment plan is to, prior to the treatment, deliver the plan on a phantom equipped with detectors measuring the deposited dose. The dose calculated based on the treatment plan is then compared to the measured one, and if they agree within a certain tolerance, the plan is deemed to be delivered as expected by the treatment machine. However, in online and real-time adaptive radiotherapy, it is not possible to measure the dose beforehand as the treatment plan is created or adapted when the patient is on the treatment couch (online) or continuously adapted in real-time in response to the changing anatomy (real-time). Given that patient QA based on measurements is not possible in the online and real-time scenarios, the dose calculation and accumulation can play a central role in the patient QA. According to the disclosed techniques, the real-time imaging together with access to the treatment machine settings during delivery of a treatment fraction can be used either offline (after the fraction has been delivered) or in real-time to calculate and accumulate the dose delivered to the patient during the delivery of the treatment fraction. In order to expedite and improve the efficiency of real-time dose computations, only a sufficient portion of the real-time imaging and treatment machine settings are considered at each dose computation. Namely, a subset of less than all of the imaging of the patient and treatment machine settings sufficient to resolve patient motion is considered in computing dose. In this way, the computed dose at each increment, while less accurate due to increased noise and smaller set of information (e.g., imaging and machine settings), is still sufficient to account for patient movement and the irradiation delivered by the treatment machine. Also, by accumulating multiple individual dose computations with lower levels of accuracy, a real-time dose accumulation with a greater level of accuracy can be determined and used to accurately represent the dose delivered to the patient during the treatment fraction.

The dose calculated in this way can then serve as verification of the treatment delivery as part of the patient QA. According to some embodiments, different levels of action can take place based on the real-time dose calculation and accumulation. For example, the treatment can be simply recorded for verification with no further action and/or the radiotherapy treatment beam can be turned OFF or ON based on the patient's organ motion and calculated dose. In some cases, the patient motion can be followed or tracked with the MLC.

In order to perform real-time dose computation and accumulation, the disclosed embodiments obtain, during delivery of a radiotherapy treatment fraction to a patient, one or more images of the patient at a first rate and generate patient motion information at a second rate based on the one or more images obtained at the first rate. Radiotherapy treatment device settings are received at a third rate during delivery of the treatment fraction and dose delivered to the patient is computed with a first level of accuracy based on the generated patient motion information and the radiotherapy treatment device settings. In some cases, the dose is computed, with a first level of accuracy, utilising an advanced Monte Carlo dose calculation that due to the speed requirements, results in a dose distribution (e.g., a 3D dose distribution) with a relatively high noise level. Such a 3D dose distribution with a first level of accuracy, by itself, is insufficient for determining dose delivered to the patient. The computed dose is used to determine during delivery of the fraction a real-time measure of accumulated dose delivered to the patient with a second greater level of accuracy. The second level of accuracy may be due to DVH metrics adding up several of the 3D dose volume elements with the first levels of accuracy. Then, by accumulating multiple individual dose computations with first levels of accuracy, a real-time dose accumulation with a greater level of accuracy (e.g., a third level of accuracy greater than the second level of accuracy) can be determined and used to accurately represent the dose delivered to the patient during the treatment fraction. As referred to herein, dose accumulation represents continuous or periodic calculation of individual dose increments of the treatment delivery where changes in patient anatomy and treatment machine settings are taken into account and that are subsequently mapped back to one common reference patient anatomy and summed up.

In some cases, the dose computations and accumulations are output at a rate (e.g., 2 Hz) that resolve patient motion, such as breathing, bowel movements, internal organ movement and deformation, and so forth. Namely, the temporal resolution of the dose accumulation can be set to 2 Hz or any other suitable value that represents the patient motion of interest. To provide dose accumulation with such a rate that resolves patient motion, real-time images of the patient that are used in the dose computations are obtained (e.g., sampled) at a rate corresponding to at least the patient motion (e.g., 2 Hz).

FIG. 1 illustrates an exemplary radiotherapy system 100 adapted to perform radiotherapy plan processing operations using one or more of the approaches discussed herein. These radiotherapy plan processing operations are performed to enable the radiotherapy system 100 to provide radiation therapy to a patient based on specific aspects of captured medical imaging data and therapy dose calculations or radiotherapy machine configuration parameters. Specifically, the following processing operations may be implemented as part of a real-time dose calculation workflow 130, implemented by treatment processing logic 120. It will be understood, however, that many variations and use cases of the following treatment processing logic 120 may be provided, including in data verification, visualization, and other medical evaluative and diagnostic settings.

The radiotherapy system 100 includes a radiotherapy processing computing system 110 which hosts treatment processing logic 120. The radiotherapy processing computing system 110 may be connected to a network (not shown), and such network may be connected to the Internet. For instance, a network can connect the radiotherapy processing computing system 110 with one or more medical information sources (e.g., a radiology information system (RIS), a medical record system (e.g., an electronic medical record (EMR)/electronic health record (EHR) system), an oncology information system (OIS)), one or more image data sources 150, an image acquisition device 170 (e.g., an imaging modality), a treatment device 180 (e.g., a radiation therapy device, also referred to herein as a radiotherapy device), and treatment data source(s) 160.

As an example, the radiotherapy processing computing system 110 can be configured to monitor current patient geometry, in real-time, to calculate dose delivery to a subject (e.g., from one or more MR images captured at a first rate, such as 5 Hz) within a given fraction. In order to expedite and increase the efficiency of dose computations, the radiotherapy processing computing system 110 samples a portion of the current patient geometry sufficient to resolve patient motion. Namely, the radiotherapy processing computing system 110 may sample the one or more MR images at a second rate, such as 2.5 Hz, to skip over every other MR image and reduce the amount of data processed by the dose computation technique. Given that the second rate of 2.5 Hz is still greater than the patient motion of 2 Hz, the reduced number of MR images still sufficiently resolves patient motion. While the patient images are obtained at the first rate during a given interval of the treatment fraction (e.g., increment of the fraction), the radiotherapy processing computing system 110 also obtains radiotherapy device settings or parameters at a third rate that is faster than the first and second rates at which the patient images are obtained (e.g., the third rate is 25 Hz). The radiotherapy processing computing system 110 may compute an effective representation of the radiotherapy device settings or parameters, that includes less than all of the information obtained at the third rate, to reduce the amount of data processed by the dose computation technique. In some cases, the effective representation may compress the radiotherapy device settings or parameters obtained at the third rate based on the second rate at which the patient images are sampled. The effective representation represents total fluence delivered from the un-compressed radiotherapy device settings or parameters. At each interval or increment of the treatment fraction, the radiotherapy processing computing system 110 computes an individual dose by applying an advanced Monte Carlo dose calculation technique to the 3D patient model determined from the sampled images and effective representation of the radiotherapy device settings to simulate radiation transport of a number of incident particles and generate a dose distribution with a noise level corresponding to a first level of accuracy.

The radiotherapy processing computing system 110 similarly samples images of the patient during a second interval or increment of the treatment fraction and computes effective radiotherapy device settings or parameters for the second interval or increment. The radiotherapy processing computing system 110 computes another dose for the second interval having the first level of accuracy and accumulates this dose with the prior computed dose. The result is a real-time dose accumulation with a second higher level of accuracy than the levels of accuracy of the individual dose computations. The radiotherapy processing computing system 110 transforms each of the plurality of dose computation to a same frame of reference of a reference geometry of the patient and accumulates each of the plurality of dose computations at a respective increment, to determine the real-time measure of accumulated dose. In some cases, each increment of accumulation increases a level of accuracy of a dosimetric index. The dosimetric index includes at least one of a quantitative single measure extracted from, for example, a 3D dose distribution or cumulated dose volume histogram (DVH), a near-maximum dose DVH measure, a near-minimum dose DVH measure, a differential DVH measure, another DVH measure, or a measure of conformity between a dose distribution and a target volume.

The radiotherapy processing computing system 110 may include processing circuitry 112, memory 114, a storage device 116, and other hardware and software-operable features such as a user interface 142, a communication interface (not shown), and the like. The storage device 116 may store transitory or non-transitory computer-executable instructions, such as an operating system, radiation therapy treatment plans (e.g., training data, treatment planning strategies, patient movement models, patient deformation models, beam delivery segment information, 3D and/or 2D image information for a patient, and device adjustment parameters, and the like), software programs (e.g., image processing software, image or anatomical visualization software, etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application-specific integrated circuit (ASIC), a field programmable gate array (FPGA), a digital signal processor (DSP), a System on a Chip (SoC), or the like.

As would be appreciated by those skilled in the art, in some examples, the processing circuitry 112 may be a special-purpose processor, rather than a general-purpose processor. The processing circuitry 112 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one physical (circuitry based) or software-based processor, for example, a multi-core design or a plurality of processors each having a multi-core design. The processing circuitry 112 can execute sequences of transitory or non-transitory computer program instructions, stored in memory 114, and accessed from the storage device 116, to perform various operations, processes, methods that will be explained in greater detail below. It should be understood that any component in radiotherapy system 100 may be implemented separately and operate as an independent device and may be coupled to any other component in radiotherapy system 100 to perform the techniques described in this disclosure.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including images, training data, ML technique parameters, device adaptation functions, data, or transitory or non-transitory computer-executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a transitory or non-transitory machine-readable medium on which is stored one or more sets of transitory or non-transitory instructions and data structures (e.g., software) embodying or utilized by any one or more of the methodologies or functions described herein (including, in various examples, the treatment processing logic 120 and the user interface 142). The instructions may also reside, completely or at least partially, within the memory 114 and/or within the processing circuitry 112 during execution thereof by the radiotherapy processing computing system 110, with the memory 114 and the processing circuitry 112 also constituting transitory or non-transitory machine-readable media.

The memory 114 and the storage device 116 may constitute a non-transitory computer-readable medium. For example, the memory 114 and the storage device 116 may store or load transitory or non-transitory instructions for one or more software applications on the computer-readable medium. Software applications stored or loaded with the memory 114 and the storage device 116 may include, for example, an operating system for common computer systems as well as for software-controlled devices. The radiotherapy processing computing system 110 may also operate a variety of software programs comprising software code for implementing the treatment processing logic 120 and the user interface 142. Further, the memory 114 and the storage device 116 may store or load an entire software application, part of a software application, or code or data that is associated with a software application, which is executable by the processing circuitry 112. In a further example, the memory 114 and the storage device 116 may store, load, and manipulate one or more radiation therapy treatment plans, imaging data, segmentation data, treatment visualizations, histograms or measurements, and the like. It is contemplated that software programs may be stored not only on the storage device 116 and the memory 114 but also on a removable computer medium, such as a hard drive, a computer disk, a CD-ROM, a DVD, a Blu-Ray DVD, USB flash drive, a SD card, a memory stick, or any other suitable medium; such software programs may also be communicated or received over a network.

Although not depicted, the radiotherapy processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, the network may be a LAN or a WAN that may include other systems (including additional image processing computing systems or image-based components associated with medical imaging or radiotherapy operations).

In an example, the radiotherapy processing computing system 110 may obtain image data 152 from the image data source 150 (e.g., CT, PET, and/or MR images), for hosting on the storage device 116 and the memory 114. In yet another example, the software programs may substitute functions of the patient images such as signed distance functions or processed versions of the images that emphasize some aspect of the image information.

In an example, the radiotherapy processing computing system 110 may obtain or communicate image data 152 from or to image data source 150. In further examples, the treatment data source 160 receives or updates the planning data 162 as a result of radiotherapy device parameter adjustments or segment adaptation generated by the real-time dose calculation workflow 130; the image data source 150 may also provide or host the image data 152 for use in the real-time dose calculation workflow 130.

The processing circuitry 112 may be communicatively coupled to the memory 114 and the storage device 116, and the processing circuitry 112 may be configured to execute computer-executable instructions stored thereon from either the memory 114 or the storage device 116. The processing circuitry 112 may execute instructions to cause medical images from the image data 152 to be received or obtained in memory 114 and processed using the treatment processing logic 120.

In addition, the processing circuitry 112 may utilize software programs to generate intermediate data such as updated parameters to be used, for example, by a neural network model, machine learning model, real-time dose calculation workflow 130, or other aspects involved with generation of device parameter adjustments or segment adaptation, as discussed herein. Further, such software programs may utilize the treatment processing logic 120 to implement the real-time dose calculation workflow 130 to produce updated radiotherapy parameters to provide to the treatment data source 160 to modify a dose delivered to a target within a given fraction and/or for presentation on output device 146, using the techniques further discussed herein. The processing circuitry 112 may subsequently then transmit the updated radiotherapy parameters via a communication interface and the network to the treatment device 180, where the updated parameters will be used to treat a patient with radiation via the treatment device 180, consistent with results of the real-time dose calculation workflow 130. Other outputs and uses of the software programs and the real-time dose calculation workflow 130 may occur with use of the radiotherapy processing computing system 110. Radiotherapy parameters (also referred to as control points) may include, for each segment or portion of a given treatment fraction, MLC positions and settings, gantry angle, radiation dose amount (e.g., amount of monitor units (MU)), radiotherapy beam direction, radiation beam size, arc placement, beam on and off time duration, machine parameters, gantry speed, MRI pulse sequence, any combination thereof, and so forth.

In an example, the image data 152 may include one or more MR images (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, 2D Cone beam CT, 3D CT, 3D CBCT, 4D CT, 4DCBCT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer-generated synthetic images (e.g., pseudo-CT images), radio-beacons, laser scanning of the patient surface, and the like. Further, the image data 152 may also include or be associated with medical image processing data, for instance, training images, and ground truth images, contoured images, and dose images. In other examples, an equivalent representation of an anatomical area may be represented in non-image formats (e.g., coordinates, mappings, etc.).

In an example, the image data 152 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise an MRI imaging device, a CT imaging device, a PET imaging device, an ultrasound imaging device, a fluoroscopic device, a SPECT imaging device, an integrated Linear Accelerator and MRI imaging device, CBCT imaging device, or other medical imaging devices for obtaining the medical images of the patient. The image data 152 may be received and stored in any type of data or any type of format (e.g., in a Digital Imaging and Communications in Medicine (DICOM) format) that the image acquisition device 170 and the radiotherapy processing computing system 110 may use to perform operations consistent with the disclosed embodiments. Further, in some examples, the models discussed herein may be trained to process the original image data format or a derivation thereof.

In an example, the image acquisition device 170 may be integrated with the treatment device 180 as a single apparatus (e.g., an MRI device combined with a linear accelerator, also referred to as an "MRI-Linac"). Such an MRI-Linac can be used, for example, to determine a location of a target in the patient, so as to direct the radiation beam accurately according to the radiation therapy treatment plan to a predetermined target. For instance, a radiation therapy treatment plan may provide information about a particular radiation dose to be applied to each patient. The radiation therapy treatment plan may also include other radiotherapy information and radiotherapy device parameters, such as beam angles, dose-volume-histogram information, the number of radiation beams to be used during therapy, the dose per beam, and the like. The MRI-Linac can be used to compute, generate, and/or update a patient deformation model to deform image portions of a 3D or 2D image of a patient corresponding to a given beam delivery segment. The MRI-Linac can be used to provide real-time patient images (or subsets of patient images) and machine settings or parameters at various increments/intervals of a treatment fraction to continuously or periodically compute dose for the increments/intervals and determine a real-time dose accumulation based on such computed doses.

The radiotherapy processing computing system 110 may communicate with an external database through a network to send/receive a plurality of various types of data related to image processing and radiotherapy operations. For example, an external database may include machine data (including device constraints) that provides information associated with the treatment device 180, the image acquisition device 170, or other machines relevant to radiotherapy or medical procedures. Machine data information may include radiation beam size, arc placement, beam on and off time duration, machine parameters, segments, MLC configuration, gantry speed, MRI pulse sequence, and the like. The external database may be a storage device and may be equipped with appropriate database administration software programs. Further, such databases or data sources may include a plurality of devices or systems located either in a central or a distributed manner.

The radiotherapy processing computing system 110 can collect and obtain data, and communicate with other systems, via a network using one or more communication interfaces, which are communicatively coupled to the processing circuitry 112 and the memory 114. For instance, a communication interface may provide communication connections between the radiotherapy processing computing system 110 and radiotherapy system components (e.g., permitting the exchange of data with external devices). For instance, the communication interface may, in some examples, have appropriate interfacing circuitry from an output device 146 or an input device 148 to connect to the user interface 142, which may be a hardware keyboard, a keypad, or a touch screen through which a user may input information into the radiotherapy system.

As an example, the output device 146 may include a display device that outputs a representation of the user interface 142 and one or more aspects, visualizations, or representations of the medical images, the treatment plans, and statuses of training, generation, verification, or implementation of such plans. The output device 146 may include one or more display screens that display medical images, interface information, treatment planning parameters (e.g., contours, dosages, beam angles, labels, maps, etc.), treatment plans, image portions that are identified and deformed for a given treatment segment, a target, localizing a target and/or tracking a target, or any related information to the user. The output device 146 may provide to a user visualization of dose accumulation based on the determined real-time measure of dose delivered to the patient during delivery of the radiotherapy treatment fraction. The visualization illustrates progress of the radiotherapy treatment fraction. In some cases, the visualization is generated by obtaining a reference dosimetric index calculated based on a reference radiotherapy treatment plan and presenting, in the visualization, the progress by graphically displaying a same dosimetric index based on the accumulated dose relative to the reference dosimetric index.

The input device 148 connected to the user interface 142 may be a keyboard, a keypad, a touch screen or any type of device using which a user may input information to the radiotherapy system 100. Alternatively, the output device 146, the input device 148, and features of the user interface 142 may be integrated into a single device such as a smartphone or tablet computer (e.g., Apple iPad®, Lenovo Thinkpad®, Samsung Galaxy®, etc.).

Furthermore, any and all components of the radiotherapy system 100 may be implemented as a virtual machine (e.g., via VMWare, Hyper-V, and the like virtualization platforms) or independent devices. For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 110, the image data sources 150, or like components, may be implemented as a virtual machine or within a cloud-based virtualization environment.

The image acquisition device 170 can be configured to acquire one or more images of the patient's anatomy for a region of interest (e.g., a target organ, a target tumour or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumour. In an example, 2D slices can be determined from information such as a 3D CBCT or CT, or MRI volume. Such 2D slices can be acquired by the image acquisition device 170 in "near real-time" while a patient is undergoing radiation therapy treatment, for example, when using the treatment device 180 (with "near real-time" meaning acquiring the data without (or with minimal) lag between image acquisition and treatment, as known in the art). In an example, 3D volumetric representation of a region of interest can be generated using a stack of one or more 2D slices.

Figure 2:
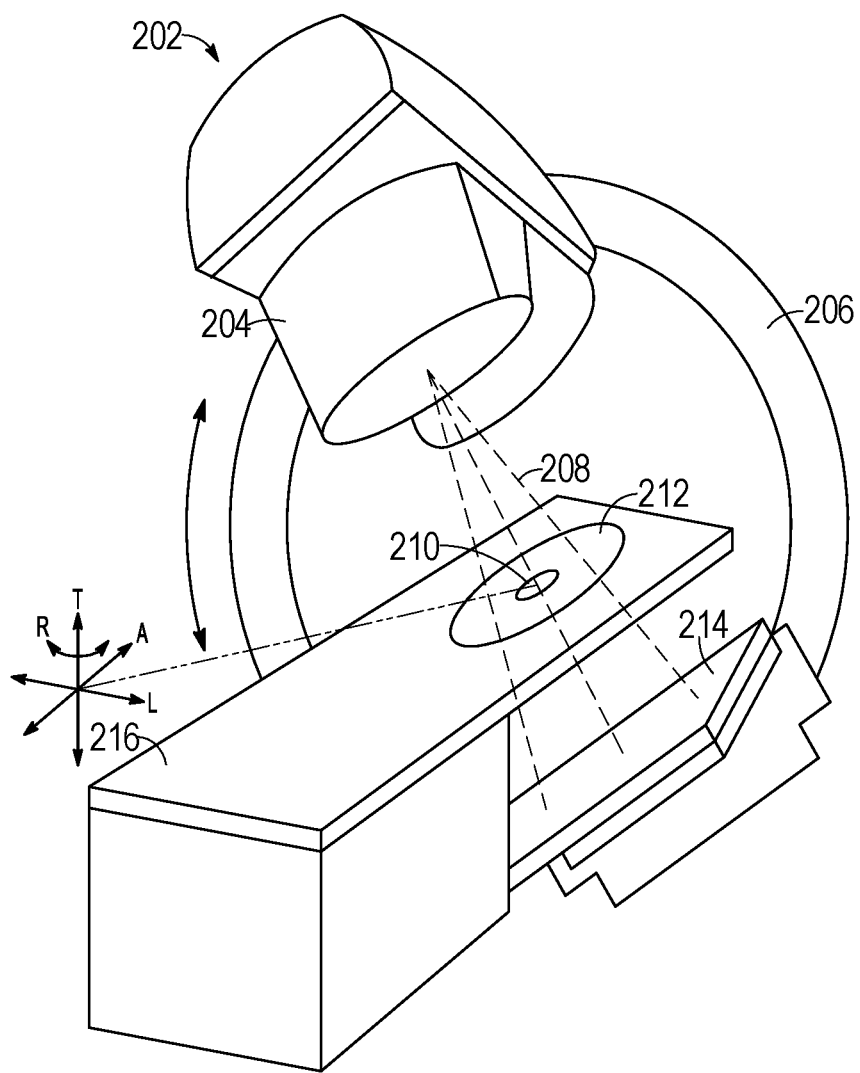
FIG. 2 is an illustrative image-guided radiotherapy device according to some examples of the disclosure.

FIG. 2 illustrates an exemplary image-guided radiation therapy device 202 that includes a radiation source, such as an X-ray source or a linear accelerator, a couch 216, an imaging detector 214, and a radiation therapy output 204. The radiation therapy device 202 may be configured to emit a radiation therapy beam 208 to provide therapy to a patient. The radiation therapy output 204 can include one or more attenuators or collimators, such as a multi-leaf collimator (MLC).

As an example, a patient can be positioned in a region 212, supported by the treatment couch 216, to receive a radiation therapy dose according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an example, gantry 206 may be continuously rotatable around couch 216 when the couch 216 is inserted into the treatment area. In another example, the gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation therapy beam 208 according to a radiation therapy treatment plan. Both the couch 216 and the gantry 206 are independently moveable from one another in multiple degrees of freedom, which allows the patient to be positioned such that the radiation therapy beam 208 can precisely target the tumour.

The coordinate system (including axes A, T, and L) can have an origin located at an isocenter 210. The isocenter 210 can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 is preferably located opposite to the radiation source (output 204), and in an example, the imaging detector 214 can be located within a field of the radiation therapy beam 208. The imaging detector 214 can be mounted on the gantry 206, preferably opposite the radiation therapy output 204, such as to maintain alignment with the radiation therapy beam 208. The imaging detector 214 rotates about the rotational axis as the gantry 206 rotates. In an example, the imaging detector 214 can be a flat panel detector (e.g., a direct detector or a scintillator detector). In this manner, the imaging detector 214 can be used to monitor the radiation therapy beam 208, or the imaging detector 214 can be used for imaging the patient's anatomy, such as portal imaging. The control circuitry of the radiation therapy device 202 may be integrated within the radiotherapy system 100 or remote from it.

In an illustrative example, one or more of the couch 216, the therapy output 204, or the gantry 206 can be automatically positioned, and the therapy output 204 can establish the radiation therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

Thus, FIG. 2 specifically illustrates an example of a radiation therapy device 202 operable to provide radiotherapy treatment to a patient consistent with or according to a radiotherapy treatment plan and parameters of a device adjusted within a given fraction, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be an MRI, an X-ray, a CT, a CBCT, a spiral CT, a PET, a SPECT, an optical tomography, a fluorescence imaging, ultrasound imaging, or radiotherapy portal imaging device, etc., as would be recognized by one of ordinary skill in the art.

Referring back to FIG. 1, the real-time dose calculation workflow 130 includes patient images information 132, a 3D patient model constructed based on those images, radiotherapy device parameters 134, and dose calculation and accumulation processing 136. In an implementation, the processes implemented by the real-time dose calculation workflow 130 may be performed in real time during a given treatment fraction (e.g., as each beam delivery segment begins or ends) and/or before or after a patient undergoes a given treatment fraction.

In an example, real-time dose calculation workflow 130 obtains a radiotherapy treatment plan for a given patient. The radiotherapy treatment plan may be generated by a clinician for delivery of radiotherapy during one or more radiotherapy treatment fractions. The radiotherapy treatment plan includes image information for the patient representing OAR(s) and a target to be irradiated. The image information may be a collection of 2D or 3D MR or CT images. The radiotherapy treatment plan also includes a plurality of radiotherapy beam delivery segments. Each beam delivery segment defines a set of radiotherapy device control points that are used throughout the radiotherapy treatment fraction. Specifically, one beam delivery segment defines a first set of control points used during a first time point or time interval of the treatment fraction and a second beam delivery segment defines a second set of control points used during a second time point or time interval of the treatment fraction that is subsequent to, prior to, and/or adjacent to the first time point. The plurality of beam delivery segments defines the beam delivery parameters that are used throughout the treatment fraction. The radiotherapy treatment plan also includes delineations of one or more of target volume(s) and/or one or more OAR(s).

In an example, the real-time dose calculation workflow 130 generates, obtains, and/or updates a patient deformation model. The patient deformation model represents an estimate or predicted movement of the patient and/or regions of the patient during an upcoming, real-time, and/or past treatment fraction. In an embodiment, the patient deformation model is generated based on at least one of one or more descriptions of the patient captured prior to or during the radiotherapy treatment fraction. The one or more descriptions may be generated based on one or more magnetic resonance (MR) images, one or more computed tomography (CT) images, one or more cone beam computed tomography (CBCT) images, surface scanning, or radio beacons. The patient deformation model may represent actual and/or estimated (predicted) patient movement at particular times or time intervals during the treatment fraction and/or throughout the treatment fraction. The patient deformation model may be provided as one or more displacement vectors.

In some embodiments, the patient images information 132 monitors current patient geometry, in real-time by capturing one or more MR images of the patient at a first rate, such as 5 Hz within a given fraction. The patient images information 132 samples a portion of the current patient geometry sufficient to resolve patient motion. In an example, the patient images information 132 samples the one or more MR images of the patient at a second rate, such as 2.5 Hz, to skip over every other MR image and reduce the amount of data processed by the dose computation technique.

While the patient images are obtained at the first rate during a given interval of the treatment fraction (e.g., increment of the fraction), the radiotherapy device parameters 134 obtains radiotherapy device settings or parameters at a third rate that is faster than the first and second rates at which the patient images are obtained (e.g., the third rate is 25 Hz). The radiotherapy device parameters 134 may compute an effective representation of the radiotherapy device settings or parameters, that includes less than all of the information obtained at the third rate, to reduce the amount of data processed by the dose computation technique. As an example, the radiotherapy device parameters 134 compresses the radiotherapy device settings obtained at the third rate into an effective representation that represents total fluence delivered from the un-compressed radiotherapy device settings or parameters.

At each interval or increment of the treatment fraction, the dose calculation and accumulation processing 136 computes an individual dose by applying an advanced Monte Carlo dose calculation technique to the sampled images and effective representation of the radiotherapy device settings to simulate radiation transport of a number of incident particles and generate a dose distribution with a noise level corresponding to a first level of accuracy. In some cases, the dose calculation and accumulation processing 136 implements a dose engine which uses a full description of the patient anatomy (geometry and tissue characterization) as well as the machine settings or control points (MLC and/or jaw positions, monitor units, gantry angle) as input. In some implementations, the dose calculation and accumulation processing 136 starts with acquiring and reconstructing a 2D image by the one or more MR patient images. The dose calculation and accumulation processing 136 applies a patient motion model to the resulting 2D image to create a motion estimate that is used by the dose engine. In some cases, the output of the motion estimate describes the patient motion relative to a reference state, $I_{REF}$.

In parallel with the image acquisition and motion estimate creation, the dose calculation and accumulation processing 136 receives treatment machine settings or control points based on the radiation being delivered to the patient at a given interval of the treatment fraction. The treatment machine settings are received as a stream of updates that contain the machine settings describing the machine state at that point in time or interval of time of the treatment fraction. The dose calculation and accumulation processing 136 deforms the patient anatomy to its current state using the motion estimate and combines the patient anatomy with the input received from the treatment machine to continuously calculate and accumulate the dose in a reference representation of the patient anatomy. For dose calculation purposes, the patient is represented as a 3D matrix of volume elements, voxels. The dose to a given voxel depends on the current geometry of the patient and the treatment machine settings defining the current radiation field. The 3D motion of the patient may be estimated based on the stream of 2D MR images of the patient that are acquired in real-time. In some cases, the 3D motion of the patient is estimated based on the sampled set of 2D images (e.g., the 2D images generated at a second rate corresponding to patient motion, such as 2.5 Hz).

The accumulated dose $D_A^{I_{REF}}(r)$ for a position r, in the reference geometry, is calculated as the sum in Equation 1 below:

$$D_A^{I_{REF}}(r) = \sum_{i=1}^{N} D_i^{I_{REF}}(r), \quad \text{(Equation 1)}$$

where N is the number of calculation iterations during the treatment and $D_i^{I_{REF}}(r)$ is the dose increment for the i:the iteration. The superscript specifies which anatomy the dose is expressed in and the subscript specifies which iteration is calculated (e.g., $D_i^{I_{REF}}(r)$ is the dose of the i:the iteration represented in the $I_{REF}$ patient anatomy). The motion estimate provides the geometrical transforms, $T^{I_{REF} \to I_i}(r)$ and $T^{I_i \to I_{REF}}(r)$, between $I_{REF}$ and $I_i$. The radiation transport during the dose calculation is performed in the anatomy of $I_i$ producing the dose distribution $D_i^{I_i}(r)$. The $D_i^{I_{REF}}(r)$ is calculated according to Equation 2 below:

$$D_i^{I_{REF}}(r) = D_i^{I_i}(T^{I_{REF} \to I_i}(r)) \quad \text{(Equation 2)}$$

Both $T^{I_{REF} \to I_i}(r)$ and $T^{I_i I_{REF}}(r)$ is represented as a deformation vector field (DVF) describing the motion of each individual voxel. In some cases, the accumulated dose $D_A^{I_{REF}}(r)$ is computed based on a sampled set of patient images (sampled at a second rate 2.5 Hz) and an effective segment that compresses multiple settings of a beam limiting device received at a third rate (e.g., 25 Hz). In such cases, the $D_i^{I_{REF}}(r)$ at each increment is computed based on Equation 5 discussed below.

Subsequently, the dose calculation and accumulation processing 136 calculates relevant characteristics such as dosimetric indices from the dose distribution and can generate a visualization representing the relevant characteristics to a user or operator. An illustrative visualization is shown and described in connection with FIG. 5.

Figure 3:
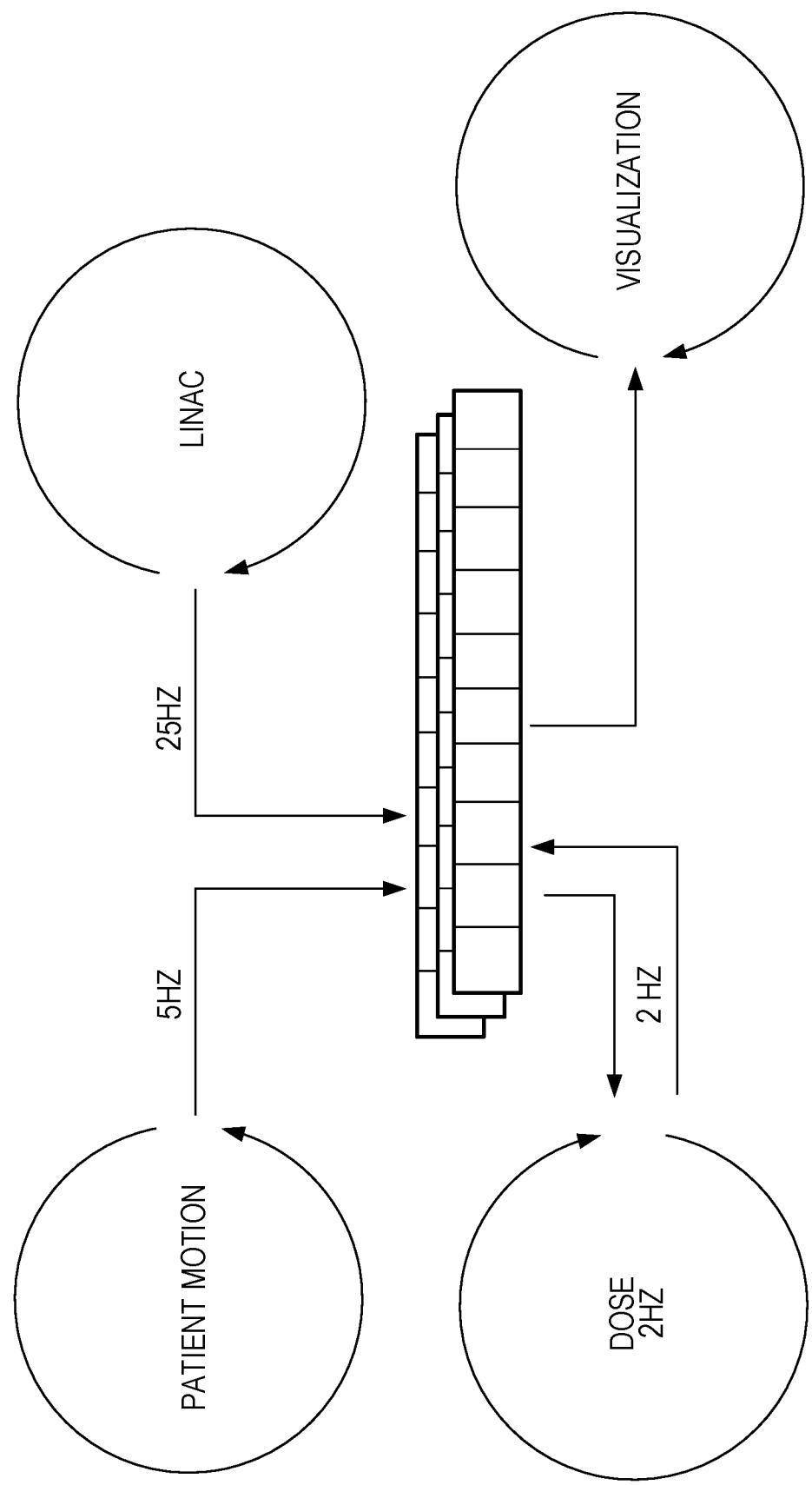
FIG. 3 is an illustrative update rate of radiotherapy treatment device components according to some examples of the disclosure.

FIG. 3 is an illustrative update rate of radiotherapy treatment device components according to some examples of the disclosure. Namely, as shown in FIG. 3, each component of the radiotherapy system 100 may provide information at different rates. As an example, the MR device or image acquisition device 170 can acquire the 2D/3D images at 5 Hz and the subsequent motion modeling processes the images at the same (or higher) speed. In this case, the motion estimates are produced at 5 Hz as well. The machine settings (Linac control points) may be streamed or received at 25 Hz. In some cases, the speed requirement for outputting and computing the dose accumulation is 2 Hz. The GUI presented to the user with the illustration of the dose accumulation provides updates to the user at a speed that is perceived as real-time which in some cases is at a rate greater than or less than 2 Hz. The disclosed embodiments cope with the cadence of the different components by sampling and using less than all of the patient motion images (e.g., 2.5 Hz of patient images) and generating an effective segment representing the total fluence delivered by the radiotherapy device corresponding to the machine settings received at 25 Hz.

In some cases, the dose calculation and accumulation processing 136 uses the position of the MLC leaves and jaws, the gantry angle, the MU delivered for the current radiation beam and the DVFs representing the motion estimate to compute dose at a given increment. Any other control points can be used to compute dose for a given increment. For notation purposes, the dose engine is defined as D(t)=D(I, TU) which calculates the dose given a patient anatomy I(t) and the treatment machine settings (control points), TU(t).

One way for handling the various sources of input data to compute dose is to pair each update of the patient motion (received at 5 Hz) with the treatment machine settings associated with the same time slot of length t. Each increment of dose in Equation 2 as a function of the patient motion state $I_i$ is based on what the treatment machine was delivering within the corresponding time slot as defined by Equation 3 below:

$$D_i^{I_i} = \int_{t_{i-1}-\frac{\Delta t}{2}}^{t_i+\frac{\Delta t}{2}} D(I_i, TU(t))dt \; i \in 1, 2, 3, \ldots, N \quad \text{(Equation 3)}$$

where TU(t) is the machine settings at time t and $I_i$ is the patient motion state at the i:th time slot. In this case, one calculation is started for every patient motion update. In cases where the dose calculation is slower than the motion estimate updates, an increasing queue of input data remains pending to be processed by the dose accumulation, which causes lag in presentation of the results to the user in the GUI.

According to some embodiments, to address this issue, the sample rate of the patient motion states is reduced by a given amount, such as by a factor of 2. This means that every second patient motion update is ignored and each increment of accumulated dose spanning a time slot of length 2Δt is computed according to Equation 4 below:

$$D_i^{I_{i-1}}(t_i) = \int_{t_{i-1}-\frac{\Delta t}{2}}^{t_i+\frac{\Delta t}{2}} D(I_{i-1}, TU(t))dt \; \epsilon \; 2, 4, 6, \ldots, N \quad \text{(Equation 4)}$$

This approximation cuts the number of iterations of the dose calculation in half and decreases the total lag of the final accumulated dose compared to the treatment progress. This enables a trade-off between sufficient sampling of the patient states and accurate calculation of the dose per iteration.

In some cases, rather than reducing the sample rate, all of the dose increment computations can be parallelized to reduce the queue of input data. In such circumstances, all of the patient motion update information is considered in computing the dose at each increment but complexity of the system resources increases.

In some embodiments, the real-time stream from the treatment device containing machine settings or control points operates at a third rate (greater than the rate at which the patient motion estimate is generated) (e.g., at 25 Hz). If the sample rate of patient motion is at a second rate of 2.5 Hz, that there will be ten updates of the treatment machine settings (segments) per increment of the dose accumulation. This will result in ten separate dose calculations, which would take too long time in the real-time context. In order to increase the efficiency of the dose computation and device and expedite the dose computation and accumulation, all queued segments of machine settings or control points are compressed into one single effective segment. To illustrate embodiment, one leaf pair of the MLC, i.e., two opposed leaves, but any other pairs of beam limiting devices (e.g., pairs of jaws and/or other pairs of MLC leaves) can be similarly compressed into an effective segment.

The stream of treatment device settings may indicate a starting position for the leaf pair at time t=0, and provide five consecutive updates with new positions and may also provide the number of MUs delivered in each update. The expansion to any number of updates is straightforward. The effective segment is computed to accurately represent the total fluence delivered from all machine settings updates, which it compresses. To generate the effective segment, the number of MUs for the effective segment is computed as the sum of all MUs in the updates. The effective segment, $S_{eff}$, is a dynamic segment in which the start and stop position of each leaf does not have to be the same. Linear motion is assumed between start and stop position of each collimating element. The start position of each leaf is chosen as the minimum and the stop position as the maximum of the positions in the updates. The dose expression for calculating each increment of the accumulated dose is then provided as Equation 5 below:

$$D_i^{I_{i-1}}(t_i) = \int_{t_{i-1}-\frac{\Delta t}{2}}^{t_i+\frac{\Delta t}{2}} D(I_{i-1}, S_{eff}(TU(t)))dt \; \epsilon \; 2, 4, 6, \ldots, N \quad \text{(Equation 5)}$$

Figure 4:
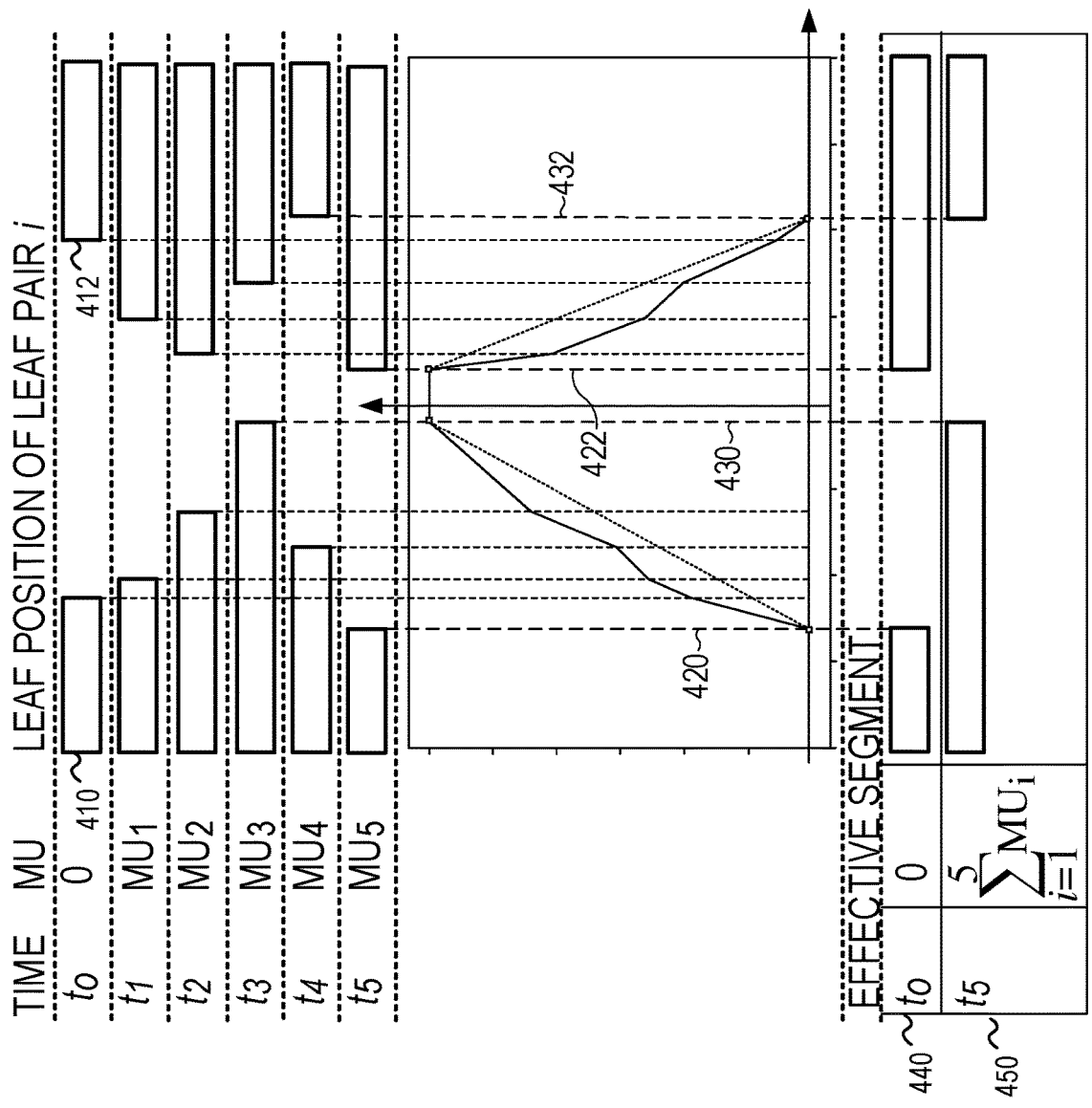
FIG. 4 is an illustrative effective beam limiting device segment representation according to some examples of the disclosure.

A graphical illustration of the creation of $S_{eff}$ from five machine updates is shown in FIG. 4, including an indication of the impact of the approximation that the method introduces. The introduction of $S_{eff}$ can both over- and underestimate the dose, mainly in the penumbra.

In some implementations, the radiotherapy device parameters 134 compresses the radiotherapy device parameters by analysing pairs of beam limiting devices. For example, the radiotherapy device parameters 134 identify a pair of leaves 410 and 412 in the set of radiotherapy device parameters of a given increment or segment corresponding to times $t_0$ to $t_5$. The radiotherapy device parameters 134 searches all of the positions of a first leaf 410 of the pair within the given times of the increment of segment to identify the minimum extended position of the first leaf 410 and the maximum extended position of the first leaf 410. The radiotherapy device parameters 134 may determine that at time $t_3$ the first leaf 410 is at a maximum extended position 430 and at time $t_5$ the first leaf 410 is at the minimum extended position 420. In response, the radiotherapy device parameters 134 may generate a first effective leaf segment that at time $t_0$ 440 starts at the minimum extended position 420 and at time $t_5$ 450 (corresponding to the last time point in the received stream of parameters) ends at the maximum extended position 430.

Similarly, the radiotherapy device parameters 134 searches all of the positions of a second leaf 412 of the pair within the given times of the increment of segment to identify the minimum extended position of the second leaf 412 and the maximum extended position of the second leaf 412. The radiotherapy device parameters 134 may determine that at time $t_5$ the second leaf 412 is at a maximum extended position 422 and at time $t_4$ the second leaf 412 is at the minimum extended position 432. In response, the radiotherapy device parameters 134 may generate a second effective leaf segment that at time to 440 starts at the minimum extended position 432 and at time $t_5$ 450 (corresponding to the last time point in the received stream of parameters) ends at the maximum extended position 422.

The radiotherapy device parameters 134 also obtains all of the MUs delivered over the given times of the increment of segment at each time point. The radiotherapy device parameters 134 sums all of the MUs delivered during the given times of the increment of segment to compute an overall MU for the effective segment from $t_0$ 440 to time $t_5$ 450. A similar technique can be applied similarly to any other type of beam limiting device pairs (e.g., jaw pairs and/or various combinations of leaf pairs) to compute one or more effective segments.

The radiotherapy device parameters 134 uses the effective segment with the overall MU as the radiotherapy device settings in computing the dose for the given increment instead of using all of the settings received from times $t_0$ to $t_5$. This reduces the overall amount of information the dose computation technique uses and expedites the output of the dose computation and accumulation.

In some cases, the dose calculation and accumulation processing 136 implements a Monte Carlo (MC) dose calculation process to compute dose and dose accumulation. The dose calculated by MC is inherently noisy where the level of noise (and hence accuracy of the calculated dose) is directly related to the number of simulated primary particles/histories used during the simulated radiation transport. The dose calculation time increases linearly with the number of simulated particles. Within MC, the patient is represented as a 3D matrix of voxels, where each voxel contains a material composition and a mass density. When calculating dose from the i:th iteration, $D_i^{I_i}$, the patient anatomy representation with material and density are deformed from $I_{REF}$ to $I_i$ using the transformation $T^{I_i \rightarrow I_{REF}}$ described by the DVF from the motion model. The density representation $\rho_i^{I_i}$ in the patient anatomy $I_i$ is calculated according to Equation 6 below:

$$\rho_i^{I_i}(r) = \rho_i^{I_{REF}}(T^{I_i \rightarrow I_{REF}}(r)) \qquad \text{(Equation 6)}$$

where the density $\rho_i^{I_i}$ is calculated using trilinear interpolation, since the density can be viewed as a continuous quantity. The material composition is treated as a discrete quantity and calculated according to Equation 7:

$$M_i^{I_i}(r) = M_i^{I_{REF}}(T^{I_i \rightarrow I_{REF}}(r)) \qquad \text{(Equation 7)}$$

and implemented using nearest neighbour interpolation. The dose per voxel is then computed as a function of $\rho_i^{I_i}(r)$ and $M_i^{I_i}(r)$.

The noise in a given voxel depends on the number of dose depositions in that voxel. DVH metrics are typically used to evaluate a 3D dose distribution, rather than dose to individual voxels and DVH metrics that consider dose to many voxels, such as $D_{2\%}$ or $D_{98\%}$ are inherently less noisy than the underlying dose distribution. Accordingly, the noise per voxel is higher for a large target than for a small target given the same level of noise in the DVH metric. As it is common to deliver homogenous dose to the target, a differential DVH will be a sharp peak around the prescribed target dose. In the case of an OAR, the case will be different since the differential DVH will have bigger spread. As a consequence of homogenous dose, the dose to the target $D_{2\%}$ or $D_{98\%}$ is more sensitive to noise than OAR metrics. According to the disclosed embodiments, the noise level of the accumulated dose decreases (i.e., the level of accuracy of the dose accumulation increases) as the dose is accumulated according to Equations 1 and 2 since the accumulation is equivalent to increasing the number of particles in the simulation. Namely, as each individual dose calculation (with a high level of noise) is accumulated with prior dose calculations (with similar high levels of noise), the overall accumulated dose computation noise decreases. In this way, the noise in the accumulated dose $D_{2\%}$ or $D_{98\%}$ starts at a high level and becomes significantly lower after a number of iterations (e.g., as more and more individual dose computations are performed and accumulated).

In some embodiments, after an individual dose is computed and accumulated with prior dose computations, the accumulated dose and/or the individual dose computation is denoised to enhance or improve the level of accuracy of the accumulated dose. The accumulated dose and/or the individual dose is denoised in parallel with a subsequent dose being computed at a subsequent iteration. In this way, while dose is computed for subsequent iterations, prior dose accumulations are denoised and improved to further reduce noise in the accumulated dose computation that is performed for subsequent iterations. Specifically, as mentioned above, each iteration of the dose calculation performed in real time during the treatment fraction produces a very noisy dose distribution $D_i^{I_{ref}}$. The noise is due to the fact that much less particles are simulated as compared to conventional dose calculations. The total dose is then accumulated according to Equation 1, which results in substantially less noise in the accumulated dose as each increment in the accumulation enables more particles to be simulated per voxel. Namely, a very noisy dose distribution can be considered because the noise in the dose distribution decreases with increments of the accumulation. Further, the full 3D dose distribution is not computed and evaluated, but rather the accumulated or differential DVH measures that are extracted from the accumulated dose resulting from Equation 1.

According to some embodiments, the differential DVH is denoised before extracting relevant DVH measures to enable increase in the speed and efficiency of the dose computation and accumulation. This is possible if the noise is known, or can be modelled, per dose level in the differential DVH. For this purpose, the noisy differential DVH $f_{noise}$ can be understood as Equation 8a below:

$$f_{noise}(D) = \int_0^\infty f_0(D')k(D'-D)dD' \quad \text{(Equation 8a)}$$

where $f_0$ is the noise free differential DVH and k a mathematical function modelling the uncertainty per dose level in the differential DVH. If k in each dose bin is known or can be modelled then the noise free DVH $f_0$ can be reconstructed by solving Equation 8a. In some embodiment, k is according to Equation 8b below:

$$k(D' - D; \sigma) = \frac{1}{\sqrt{2\pi}\sigma(D')} e^{-(D'-D)^2/2\sigma^2(D')} \quad \text{(Equation 8b)}$$

where σ is a function proportional to the square root of the dose level.

According to the disclosed embodiments, the noise free DVH is reconstructed by employing an optimization problem where bounds are set on the differential DVH to ensure non-negativity.

The optimization problem is set up as the least squares minimization problem where the blurred estimated noiseless signal (Equation 8a discretized into dose bins) represented by Equation 10 below:

$$\phi_i = \sum_{j=0}^{N} f_j k(D_j - D_i; \sigma)\Delta D$$

where $f_j$ is the discretized $f_0$. The error function to be minimized is represented by Equation 11:

$$\chi^2 = \sum_{i=0}^{N} (\phi_i - f_{noise}(D_i))^2 \quad \text{(Equation 11)}$$

Instead of employing an iterative method to solve the optimization problem, the minimization of the least square problem is solved according to Equation 12:

$$\min_f \chi^2 \quad \text{(Equation 12)}$$
$$\text{s.t. } f_j \geq 0, \quad j = 0 \ldots N$$

using an optimization where bounds on $f_j$ can be set (e.g., the L-BFGS-B method) to ensure non-negativity of the resulting denoised differential DVH. In some embodiments, offline intra-fraction dose accumulation can be used after a treatment fraction has been delivered to perform patient QA on the delivered treatment fraction. The offline intra-fraction dose accumulations may be complete MC applied to logged patient movement information and machine parameters of the delivered treatment fraction. Namely, after the treatment fraction is delivered, all patient movement information throughout the treatment fraction and all the corresponding machine parameters may be obtained from a log file. The conventional MC may then be applied to obtain the accumulated dose for the treatment fraction using the obtained patient movement information and machine parameters to compute the accumulated dose with a high level of accuracy. Namely, after the treatment fraction is delivered, there is no need to perform approximations of the patient movement information and the machine parameters (e.g., the effective segment of the beam limiting device) but rather all such information can be considered. This is because time is not of the essence and full calculations can be performed to obtain a very accurate dose accumulation as long as such calculations are completed before delivery of another treatment fraction. In some cases, the log files that store the machine parameters are updated every 40 milliseconds during treatment to be used in the offline dose accumulation. Also, the patient motion can be recreated using a log of 2D or 3D images captured during the treatment fraction. Pairing the machine settings with the concurrent patient motion constitutes the dose accumulation input for each increment. The total summed up dose of all the increments of the fraction can then be compared with the dose calculated based on the online treatment plan and used as a patient QA method to verify that the dose delivered to the patient corresponds to what was intended.

In some cases, the total dose for a given increment or for all the increments can be compared with the estimated dose accumulation that was computed in real time based on the patient geometry and machine parameter approximations. This allows for QA of the approximations made during real-time dose accumulations during the prior treatment fractions and potentially used to alter approximations of the patient geometry and machine parameters considered during delivery of a subsequent treatment fraction. Namely, 3D distributions of dose accumulated offline intra-fraction and inter-fraction dose accumulations can be used to adapt subsequent fractions (e.g., to be used as a basis for offline adaptation). For example, a user may be given the opportunity to compensate for any hot or cold spots in the current total dose distribution (e.g., smaller sets of voxels where the dose deviates from the desired homogenous interval).

Figure 5:
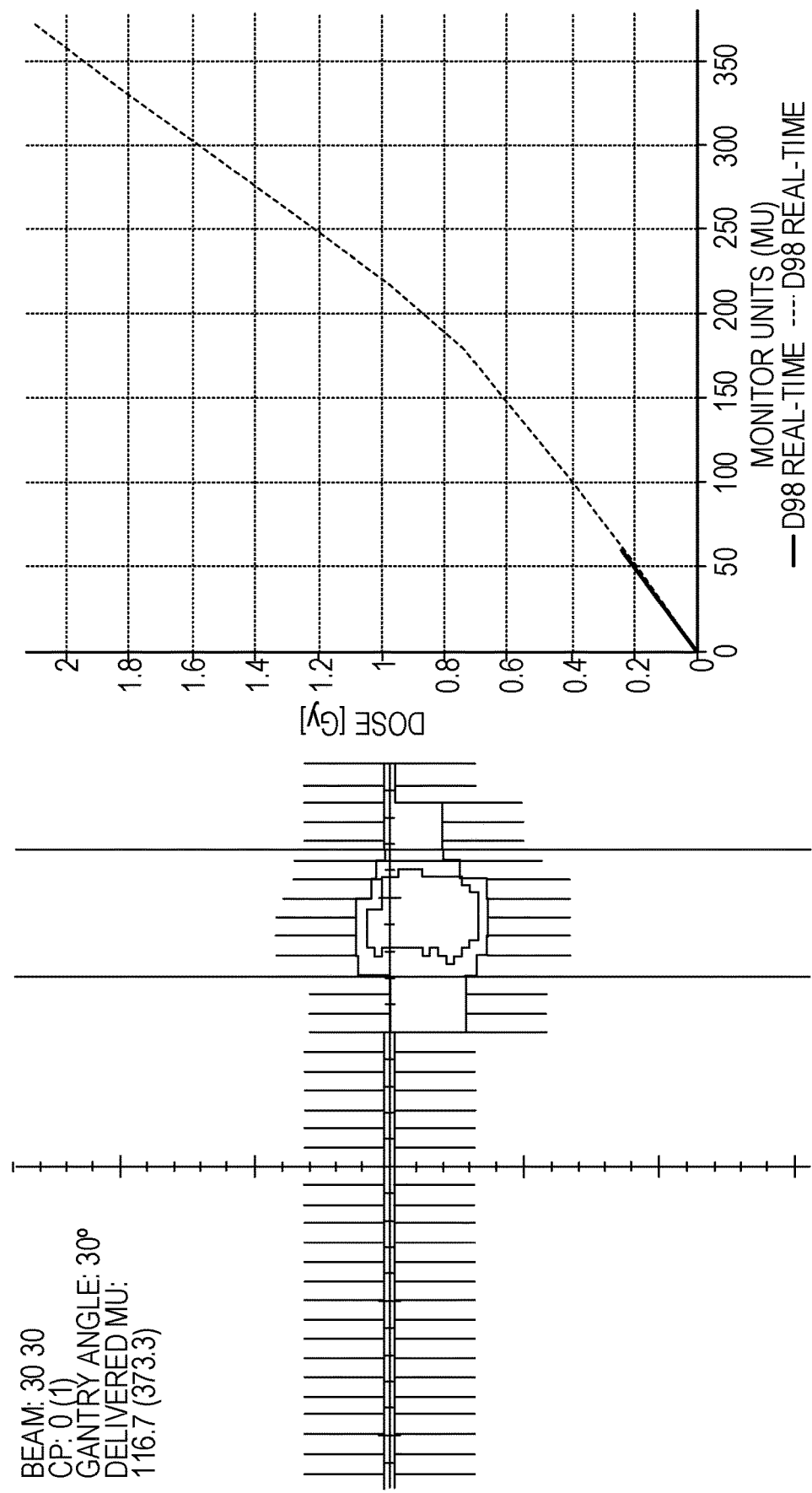
FIG. 5 is an illustrative visualization of dose accumulation according to some examples of the disclosure.

In some embodiments, the real-time dose accumulation is presented to a user in a graphical user interface during delivery of a treatment fraction to inform the user about progress of treatment. FIG. 5 is an illustrative visualization of dose accumulation according to some examples of the disclosure. The visualization may include two portions. A first portion on the left of the visualization, for example, may graphically depict the target projection and the beam limiting device (e.g., MLC) positions from the beams-eye-view in real time. Concurrently, in a second portion on the right of the visualization, the accumulated dose for the reference geometry is presented as a function of the MU. This enables the user to visually see how the accumulated dose computation compares to the target dose according to a treatment plan as the treatment progresses. In some cases, the dosimetric measures that are displayed are the same or a subset of the measures that are used to evaluate the treatment plan during planning. In some implementations, the second portion of the visualization presents the dosimetric measure $D_{98\%}(MU)$ calculated for the static reference treatment plan on the reference patient geometry so the treatment progress can be compared and validated.

In some embodiments, the beam may be gated (turned ON/OFF) automatically or manually based on how the currently computed real-time accumulated dose compares with the dosimetric measure calculated based on the static reference plan and patient geometry. Namely, if the real-time accumulated dose exceeds the reference dosimetric measure by more than a threshold amount, the beam may be turned OFF for a given portion of the treatment fraction automatically or manually. In addition, or alternatively, MLC tracking may be performed based on how the currently computed real-time accumulated dose compares with the dosimetric measure calculated based on the static reference plan and patient geometry. The MLC tracking may, in some cases, only use the geometrical input.

Figure 6:
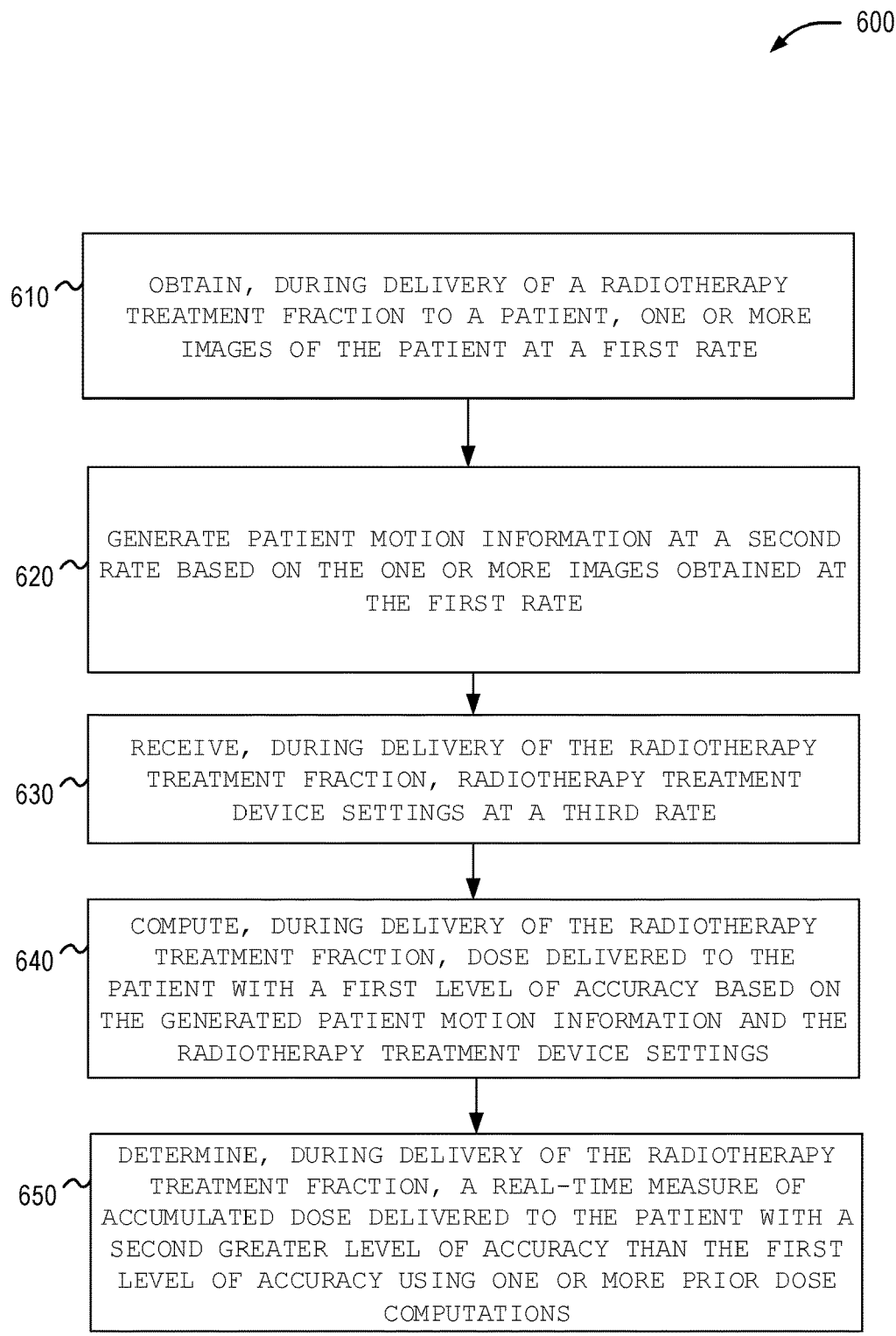
FIG. 6 illustrates a flowchart of exemplary operations for performing real-time dose calculations during a radiotherapy treatment fraction according to some examples of the disclosure.

FIG. 6 is a flowchart illustrating example operations of the real-time dose calculation workflow 130 in performing process 600, according to example embodiments. The process 600 may be embodied in computer-readable instructions for execution by one or more processors such that the operations of the process 600 may be performed in part or in whole by the functional components of the treatment processing logic 120; accordingly, the process 600 is described below by way of example with reference thereto. However, in other embodiments, at least some of the operations of the process 600 may be deployed on various other hardware configurations. The process 600 is therefore not intended to be limited to the treatment processing logic 120 and can be implemented in whole, or in part, by any other component. Some or all of the operations of process 600 can be in parallel, out of order, or entirely omitted.

At operation 610, treatment processing logic 120 obtains, during delivery of a radiotherapy treatment fraction to a patient, one or more images of the patient at a first rate.

At operation 620, treatment processing logic 120 generates patient motion information at a second rate based on the one or more images obtained at the first rate.

At operation 630, treatment processing logic 120 receives, during delivery of the radiotherapy treatment fraction, radiotherapy treatment device settings at a third rate.

At operation 640, treatment processing logic 120 computes, during delivery of the radiotherapy treatment fraction, dose delivered to the patient with a first level of accuracy based on the generated patient motion information and the radiotherapy treatment device settings.

At operation 650, treatment processing logic 120 determines, during delivery of the radiotherapy treatment fraction, a real-time measure of accumulated dose delivered to the patient with a second greater level of accuracy than the first level of accuracy using one or more prior dose computations.

As previously discussed, respective electronic computing systems or devices may implement one or more of the methods or functional operations as discussed herein. In one or more embodiments, the radiotherapy processing computing system 110 may be configured, adapted, or used to control or operate the image-guided radiation therapy device 202, perform or implement the operations of the process 600, or perform any one or more of the other methodologies discussed herein. In various embodiments, such electronic computing systems or devices operate as standalone devices or may be connected (e.g., networked) to other machines. For instance, such computing systems or devices may operate in the capacity of a server or a client machine in server-client network environment, or as a peer machine in a peer-to-peer (or distributed) network environment. Features of computing systems or devices may be embodied by a personal computer (PC), a tablet PC, a Personal Digital Assistant (PDA), a cellular telephone, a web appliance, or any machine capable of executing instructions (sequential or otherwise) that specify actions to be taken by that machine.

As also indicated above, the functionality discussed above may be implemented by instructions, logic, or other information storage on a machine-readable medium. While the machine-readable medium may have been described in various examples with reference to be a single medium, the term "machine-readable medium" may include a single medium or multiple media (e.g., a centralized or distributed database, and/or associated caches and servers) that store the one or more transitory or non-transitory instructions or data structures. The term "machine-readable medium" shall also be taken to include any tangible medium that is capable of storing, encoding or carrying transitory or non-transitory instructions for execution by the machine and that cause the machine to perform any one or more of the methodologies of the present inventive subject matter, or that is capable of storing, encoding or carrying data structures utilized by or associated with such instructions.

The above detailed description includes references to the accompanying drawings, which form a part of the detailed description. The drawings show, by way of illustration but not by way of limitation, specific embodiments in which the inventive subject matter can be practiced. These embodiments are also referred to herein as "examples." Such examples can include elements in addition to those shown or described. However, this disclosure also contemplates examples in which only those elements shown or described are provided. Moreover, the disclosure also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the inventive subject matter or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present inventive subject matter also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the inventive subject matter.

In view of the above, it will be seen that the several objects of the inventive subject matter are achieved and other beneficial results attained. Having described aspects of the inventive subject matter in detail, it will be apparent that modifications and variations are possible without departing from the scope of aspects of the inventive subject matter as defined in the appended claims. As various changes could be made in the above constructions, products, and methods without departing from the scope of aspects of the inventive subject matter, it is intended that all matter contained in the above description and shown in the accompanying drawings shall be interpreted as illustrative and not in a limiting sense.

The examples described herein may be implemented in a variety of embodiments. For example, one embodiment includes a computing device including processing hardware (e.g., a processor or other processing circuitry) and memory hardware (e.g., a storage device or volatile memory) including instructions embodied thereon, such that the instructions, when executed by the processing hardware, cause the computing device to implement, perform, or coordinate the electronic operations for these techniques and system configurations. Another embodiment discussed herein includes a computer program product, such as may be embodied by a machine-readable medium or other storage device, which provides the transitory or non-transitory instructions to implement, perform, or coordinate the electronic operations for these techniques and system configurations. Another embodiment discussed herein includes a method operable on processing hardware of the computing device to implement, perform, or coordinate the electronic operations for these techniques and system configurations.

In further embodiments, the logic, commands, or transitory or non-transitory instructions that implement aspects of the electronic operations described above, may be provided in a distributed or centralized computing system, including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described above, or other aspects depicted in the accompanying drawings and detailed description below.

The above description is intended to be illustrative, and not restrictive. For example, the above-described examples (or one or more aspects thereof) may be used in combination with each other. In addition, many modifications may be made to adapt a particular situation or material to the teachings of the present disclosure without departing from its scope. While the dimensions, types of materials and example parameters, functions, and implementations described herein are intended to define the parameters of the inventive subject matter, they are by no means limiting and are exemplary embodiments. Many other embodiments will be apparent to those of skill in the art upon reviewing the above description. The scope of the inventive subject matter should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the inventive subject matter should be determined with reference to the appended claims, along with the full scope of equivalents to which such claims are entitled.

What is claimed is:

1. A method comprising:
   obtaining, by one or more processors, during delivery of a radiotherapy treatment fraction to a patient, one or more images of the patient at a first rate;
   generating patient motion information at a second rate based on the one or more images obtained at the first rate by sampling the one or more images at the second rate that is lower than the first rate;
   receiving, during delivery of the radiotherapy treatment fraction, radiotherapy treatment device settings at a third rate that is greater than the first rate;
   computing, during delivery of the radiotherapy treatment fraction, a first measure of accumulated dose delivered to the patient, the first measure of accumulated dose that is computed having a first amount of noise, and the first measure of accumulated dose being computed based on the generated patient motion information and the radiotherapy treatment device settings; and
   using one or more prior dose computations comprising the first measure of accumulated dose having the first amount of noise, determining, at a rate lower than the first rate, during delivery of the radiotherapy treatment fraction, a second measure of accumulated dose delivered to the patient with a lower amount of noise than the first measure of accumulated dose, an overall accumulated dose computation noise being reduced as each individual measure of accumulated dose is accumulated with prior dose measure calculations.

2. The method of claim 1, further comprising:
   determining a fourth rate at which dose is computed and accumulated, the fourth rate being lower than the first rate; and
   setting the second rate at which the one or more images are sampled based on the fourth rate at which the dose is computed.

3. The method of claim 2, further comprising:
   setting the second rate that corresponds to motion of the patient; and
   skipping a set of images of a plurality of images, obtained at the first rate, to reduce amount of data processed to compute the first measure of accumulated dose.

4. The method of claim 1, wherein the dose is computed using an advanced Monte Carlo dose calculation technique resulting in a dose distribution with a noise level corresponding to the first amount of noise.

5. The method of claim 1, wherein the dose is computed at a fourth rate such that each of a plurality of dose computations for the radiotherapy treatment fraction is output at the fourth rate, each of the plurality of dose computations individually having a level of noise lower than prior dose computations, further comprising: transforming each of the plurality of dose computation to a same frame of reference of a reference geometry and accumulating each of the plurality of prior dose computations at a respective increment, to determine a real-time measure of accumulated dose, wherein each increment of accumulation decreases noise present in a dosimetric index.

6. The method of claim 5, wherein the second rate is set to a value that sufficiently resolves motion patterns of the patient.

7. The method of claim 6, further comprising calculating the dosimetric index by extracting a subset of 3D portions of 3D Monte Carlo dose calculations.

8. The method of claim 5, wherein the dosimetric index includes at least one of a quantitative single measure extracted from a 3D dose distribution, a near-maximum dose, a near-minimum dose, or a measure of conformity between a dose distribution and a target volume.

9. The method of claim 5, wherein the dosimetric index includes a dose value histogram (DVH) or a DVH measure.

10. The method of claim 1, further comprising:
obtaining a stream of the radiotherapy treatment device settings corresponding to a given time interval of the radiotherapy treatment fraction;
compressing, into a single effective segment, the stream of the radiotherapy treatment device settings, the single effective segment representing positioning of beam limiting device (BLD) elements throughout the given time interval and a number of monitor units (MU) delivered throughout the given time interval; and
computing the first measure of accumulated dose delivered to the patient based on the single effective segment.

11. The method of claim 10, wherein the radiotherapy treatment device settings received at the third rate comprises a set of updates to the radiotherapy treatment device settings performed during the given time interval of the radiotherapy treatment fraction corresponding to the third rate, further comprising aggregating into the single effective segment a total fluence delivered by a plurality of beam delivery segments.

12. The method of claim 11, wherein the single effective segment comprises a start and a stop position of every pair of BLD elements, wherein computing the effective segment comprises, for every pair of BLD elements:
obtaining all positions of the pair of BLD elements for each of the set of updates;
identifying a maximum position of each pair of BLD elements in a current pair of BLD elements among the obtained positions in the set of updates;
identifying a minimum position of each pair of BLD elements in the current pair of BLD elements among the obtained positions in the set of updates;
assigning the minimum position as a starting position for each pair of BLD elements in the current pair of BLD elements; and
assigning the maximum position as a stopping position for each pair of BLD elements in the current pair of BLD elements.

13. The method of claim 12, wherein the pair of BLD elements comprises at least one of a pair of jaws of a multi-leaf collimator (MLC) or a pair of leaves of the MLC, further comprising:
determining a number of MUs delivered for each of the set of updates;
accumulating the determined number of MUs for the set of updates to compute a total fluence; and
assigning the accumulated determined number of MUs to the effective segment.

14. The method of claim 1, further comprising generating, at a fourth rate, a visualization of dose accumulation based on the second measure of accumulated dose.

15. The method of claim 14, wherein the visualization illustrates real-time progress of the radiotherapy treatment fraction, further comprising:
obtaining a reference dosimetric index calculated based on a reference radiotherapy treatment plan; and
presenting, in the visualization, the real-time progress by graphically displaying a same dosimetric index based on the accumulated dose relative to the reference dosimetric index.

16. The method of claim 1, further comprising:
obtaining all positions of beam limiting device (BLD) elements for a set of updates;
identifying a maximum and minimum positions associated with the BLD elements; and
using the maximum and minimum positions to identify starting and ending positions for the BLD elements in the set of updates.

17. The method of claim 16, further comprising computing an effective segment based on the starting and ending positions of the BLD elements in the set of updates, the effective segment being used to compute the first measure of accumulated dose.

18. The method of claim 16, further comprising accumulating a number of monitor units (MUs) delivered during a given interval based on the set of updates to compute a total fluence and assigning the accumulated number of MUs to an effective segment that is used to compute the first measure of accumulated dose.

19. A system for adjusting radiotherapy treatment for a patient in real time, the system comprising:
one or more processors for performing operations comprising:
obtaining, during delivery of a radiotherapy treatment fraction to a patient, one or more images of the patient at a first rate;
generating patient motion information at a second rate based on the one or more images obtained at the first rate;
receiving, during delivery of the radiotherapy treatment fraction, radiotherapy treatment device settings at a third rate;
computing, during delivery of the radiotherapy treatment fraction, a first measure of accumulated dose delivered to the patient, the first measure of accumulated dose that is computed having a first amount of noise, and the first measure of accumulated dose being computed based on the generated patient motion information and the radiotherapy treatment device settings; and
using one or more prior dose computations comprising the first measure of accumulated dose having the first amount of noise, determining, at a rate lower than the first rate, during delivery of the radiotherapy treatment fraction, a second measure of accumulated dose delivered to the patient with a lower amount of noise than the first measure of accumulated dose, an overall accumulated dose computation noise being reduced as each individual measure of accumulated dose is accumulated with prior dose measure calculations.

20. A non-transitory computer-readable medium encoded with computer-readable instructions that, when executed by one or more processors, configure the one or more processors to perform operations comprising:

obtaining during delivery of a radiotherapy treatment fraction to a patient, one or more images of the patient at a first rate;

generating patient motion information at a second rate based on the one or more images obtained at the first rate by sampling the one or more images at the second rate that is lower than the first rate;

receiving, during delivery of the radiotherapy treatment fraction, radiotherapy treatment device settings at a third rate that is greater than the first rate;

computing, during delivery of the radiotherapy treatment fraction, a first measure of accumulated dose delivered to the patient, the first dose that is computed having a first amount of noise, and the first dose being computed based on the generated patient motion information and the radiotherapy treatment device settings;

computing, during delivery of the radiotherapy treatment fraction, a first measure of accumulated dose delivered to the patient, the first measure of accumulated dose that is computed having a first amount of noise, and the first measure of accumulated dose being computed based on the generated patient motion information and the radiotherapy treatment device settings; and using one or more prior dose computations comprising the first measure of accumulated dose having the first amount of noise, determining, at a rate lower than the first rate, during delivery of the radiotherapy treatment fraction, a second measure of accumulated dose delivered to the patient with a lower amount of noise than the first measure of accumulated dose, an overall accumulated dose computation noise being reduced as each individual measure of accumulated dose is accumulated with prior dose measure calculations.

\* \* \* \* \*